United States Patent
Shikaumi et al.

(10) Patent No.: US 8,393,736 B2
(45) Date of Patent: Mar. 12, 2013

(54) OPHTHALMIC IMAGING APPARATUS, IMAGING UNIT, INSPECTION APPARATUS, AND METHOD OF PRODUCING OPHTHALMIC IMAGING APPARATUS

(75) Inventors: Masao Shikaumi, Tokyo (JP); Yasuhiro Nakahara, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 143 days.

(21) Appl. No.: 12/892,798

(22) Filed: Sep. 28, 2010

(65) Prior Publication Data
US 2011/0090457 A1    Apr. 21, 2011

(30) Foreign Application Priority Data
Oct. 20, 2009   (JP) ................................ 2009-241697

(51) Int. Cl.
*A61B 3/14* (2006.01)
*A61B 3/00* (2006.01)

(52) U.S. Cl. ....................................... 351/206; 351/246
(58) Field of Classification Search .......... 351/200–246
See application file for complete search history.

(56) References Cited

U.S. PATENT DOCUMENTS

| | | | | |
|---|---|---|---|---|
| 4,717,952 A | * | 1/1988 | Kohayakawa et al. | 348/164 |
| 6,488,377 B2 | * | 12/2002 | Matsumoto | 351/206 |
| 6,648,472 B1 | * | 11/2003 | Mizuochi | 351/206 |

FOREIGN PATENT DOCUMENTS

JP   62-94134 A    4/1987

* cited by examiner

*Primary Examiner* — Mohammed Hasan
(74) *Attorney, Agent, or Firm* — Canon U.S.A., Inc., IP Division (57) ABSTRACT

A method of producing an ophthalmic imaging apparatus includes the steps of producing an imaging unit configured to capture an image of an image subject in visible light and infrared light; adjusting the color tone of the imaging unit using a color-tone adjustment unit having a first optical member configured to absorb infrared light; and connecting the adjusted imaging unit and an optical system having a second optical member whose characteristic is the same as a characteristic of the first optical member and configured to capture an optical image of an eye to be examined.

20 Claims, 10 Drawing Sheets

OPHTHALMIC IMAGING APPARATUS, IMAGING UNIT, INSPECTION APPARATUS, AND METHOD OF PRODUCING OPHTHALMIC IMAGING APPARATUS

BACKGROUND OF THE INVENTION

1. Field of the Invention

The present invention relates to a method of producing an ophthalmic imaging apparatus configured to capture an image of an image subject in visible light and infrared light, an inspection apparatus used for production, an ophthalmic imaging apparatus, and an imaging unit.

2. Description of the Related Art

Fundus cameras are used to capture images of the ocular fundus for the purpose of, for example, diagnosing the ocular fundus and performing diabetes examinations. With a non-mydriatic fundus camera, the ocular fundus is irradiated with infrared light to carry out positioning and focusing and then irradiated with visible light to capture the reflected light as an optical image of the ocular fundus. The digital data can be used in various ways, such as in fundus examination and in digitally storing image data. One type of such fundus cameras includes an image sensor sensitive to visible light and infrared light. Such fundus camera captures images in visible light and infrared light by inserting an infrared-blocking filter, which covers the entire surface of an image sensor, into an optical path during examination and by removing the filter from the optical path during image capturing.

To improve the performance of image sensors, the image sensors are modified at a fast pace. As a result, characteristics, such as color tone, of the image sensors differ for each model number. Therefore, when the characteristics, such as color tone, of the entire fundus camera are adjusted, it is difficult to adjust the characteristics of the image sensor because they are influenced by the variation in the optical systems in the fundus camera.

SUMMARY OF THE INVENTION

The present invention produces an ophthalmic imaging apparatus in such a manner that corresponds to changes in the characteristics due to modifications of an imaging unit.

In one embodiment of the present invention, there is provided a method of producing an ophthalmic imaging apparatus including the steps of producing an imaging unit configured to capture an image of an image subject in visible light and infrared light; adjusting the color tone of the imaging unit using a color-tone adjustment unit having a first optical member configured to absorb infrared light; and connecting the adjusted imaging unit and an optical system having a second optical member whose characteristic is the same as a characteristic of the first optical member and configured to capture an optical image of an eye to be examined.

Further features of the present invention will become apparent from the following description of exemplary embodiments with reference to the attached drawings.

DESCRIPTION OF THE EMBODIMENTS

First Embodiment

This embodiment describes a fundus camera that converts a fundus optical image to digital data using a digital single-lens reflex camera, which is a visible-light imaging apparatus, allowing infrared light to reach the image pick-up element.

Figure 1:
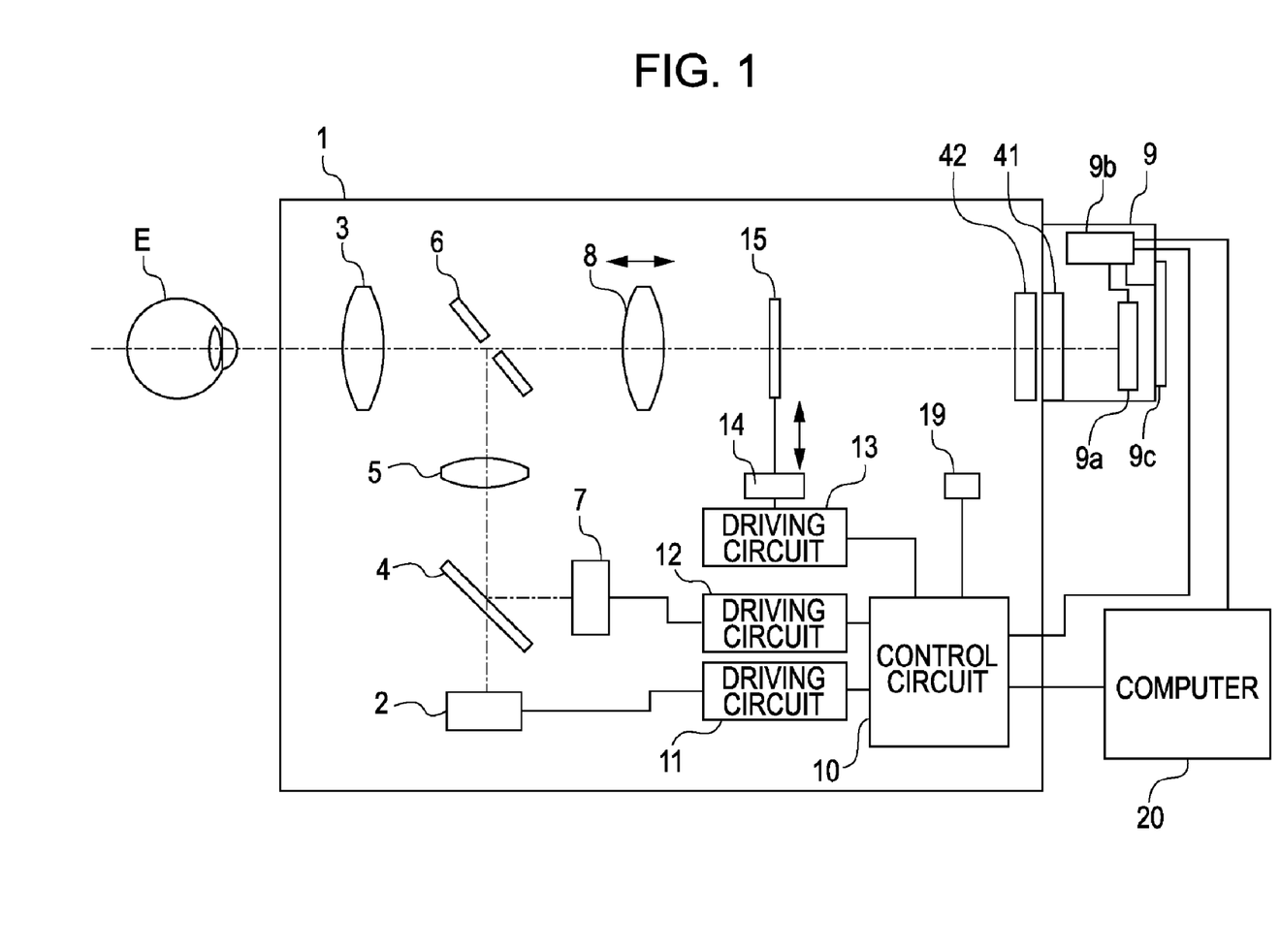
FIG. 1 illustrates an ophthalmic imaging apparatus.

FIG. 1 illustrates an ophthalmic imaging apparatus. This ophthalmic imaging apparatus includes a fundus camera 1 that captures an optical image of the ocular fundus of the eye to be examined and an imaging unit that receives the optical image as digital data. The fundus camera 1 functions as a capturing unit that captures an optical image of the ocular fundus of the eye to be examined, which is an image subject. The fundus camera according to this embodiment is a non-mydriatic fundus camera. The fundus camera 1 disposed in front of the image subject, i.e., an eye E to be examined, accommodates an examination illumination optical system from an examination light source 2 that emits infrared light generated at, for example, an infrared LED to an objective lens 3 disposed with respect to the eye E. This examination illumination optical system includes the examination light source 2, a dichroic mirror 4, a relay lens 5, and a perforated mirror 6, which are arranged in this order. An imaging light source 7 having a xenon tube as an imaging illumination optical system is disposed in the incidence direction of the dichroic mirror 4.

A focusing lens 8, which is part of an imaging optical system, adjusts the focus by moving along the optical axis and is disposed after the perforated mirror 6. A digital single-lens reflex camera 9 is attached to the fundus camera 1 in a detachable manner on a line extending from the optical axis of the focusing lens 8.

The digital single-lens reflex camera 9 is an imaging unit that creates digital image data by converting an optical image formed by the incident imaging light (infrared light and visible light) to an electrical signal. The digital image data is stored and used for diagnosis and recording, as well as being displayed during image capturing for examination. The digital single-lens reflex camera 9, which is an imaging unit capturing a fundus optical image, is produced by partially modifying the optical system of a regular digital single-lens reflex camera for visible-light imaging. Therefore, the external appearance and configuration of the digital single-lens reflex camera 9 are the same as those of a regular digital single-lens reflex camera for visible-light imaging.

The digital single-lens reflex camera 9, which is an imaging unit, does not necessarily have to include a reflective mirror, and may display on a viewfinder a digital image acquired by the image sensor. The digital single-lens reflex camera 9, which is an imaging unit, has a lens joining unit 41 that detachably holds an objective lens for guiding an optical image of an image subject as imaging light to an image sensor 9a. The lens joining unit 41 joins the digital single-lens reflex camera 9 with the fundus camera 1. The fundus camera 1 has a camera joining unit 42 that joins with the lens joining unit 41. The camera joining unit 42 and the lens joining unit 41 enable the digital single-lens reflex camera 9 to acquire, as digital data, an optical image of the ocular fundus of the eye captured by the fundus camera 1.

The digital single-lens reflex camera 9 accommodates the image sensor 9a, which receives imaging light and converts an optical image formed on its surface to an electrical signal. The output of the image sensor 9a is connected to a control unit 9b in the digital single-lens reflex camera 9. A liquid crystal display 9c, which is a display unit, is disposed on the back side of the digital single-lens reflex camera 9 and is connected to the output of the control unit 9b. The digital single-lens reflex camera 9 according to this embodiment does not include an infrared-blocking optical member, which is normally disposed in front of the image sensor 9a, for the purpose of providing near-infrared sensitivity. The image sensor 9a is capable of receiving visible light and infrared light and acquiring image data. Details will be described below.

The fundus camera 1 accommodates a control circuit 10 of which the outputs are connected to the examination light source 2 and the imaging light source 7 via driving circuits 11 and 12, respectively. The control circuit 10 is also connected to the control unit 9b in the digital single-lens reflex camera 9 and to a release switch 19 provided on the fundus camera 1.

Moreover, the control circuit 10 is connected to an actuator 14 via the driving circuit 13. The actuator 14 is driven to insert or retract an infrared blocking filter 15 into and from an imaging optical path. The infrared blocking filter 15 has the same infrared blocking ability as that of the optical member not included in the digital single-lens reflex camera 9. By retracting the infrared blocking filter 15 from the imaging optical path during examination, an image of the ocular fundus can be examined by the digital single-lens reflex camera 9. By inserting the infrared blocking filter 15 into the imaging optical path during image capturing, the digital single-lens reflex camera 9 and the infrared blocking filter 15 acquires the same spectral characteristic as that of a regular digital single-lens reflex camera for visible-light imaging.

Furthermore, the control circuit 10 includes a one-chip microcomputer and so on and records various adjustment values in an embedded or external non-volatile memory (not shown). Adjustment values for compensating the infrared blocking ability of the infrared blocking filter 15, as described below, are also stored in this non-volatile memory.

A computer 20 is provided outside the fundus camera 1 and is connected to the control unit 9b of the digital single-lens reflex camera 9 and the control circuit 10 of the fundus camera 1 via USB or a serial port. Development parameters for examination and image capturing are stored in the computer 20 in advance for image forming by different models of the digital single-lens reflex camera 9 that can be connected to the fundus camera 1. Such development parameters are stored in advance because the characteristic of the image sensor 9a and the spectral characteristic of the color filters attached to the surface differ for each model, and the image processing parameters should be changed in accordance with the model.

When the release switch 19 is pushed, the control circuit 10 transmits a release signal to the control unit 9b of the digital single-lens reflex camera 9, causing the digital single-lens reflex camera 9 to carry out operation for image capturing.

Many recent models of digital single-lens reflex cameras have a live view function. Live view is a function of retracting a quick return mirror embedded in the digital single-lens reflex camera 9, opening the shutter, sequentially reading out images formed on the image sensor 9a, and sequentially displaying the images on the liquid crystal display 9c, which is a display unit, on the back side of the camera. The digital single-lens reflex camera 9 has such a live view function and is capable of displaying images on the display unit during image capturing. The display unit may be the viewfinder of the digital single-lens reflex camera 9.

In this embodiment, during examination, the digital single-lens reflex camera 9 uses the live view function.

Next, how the infrared blocking ability is eliminated from the digital single-lens reflex camera 9 according to this embodiment is described with reference to FIG. 2.

Figure 2A:
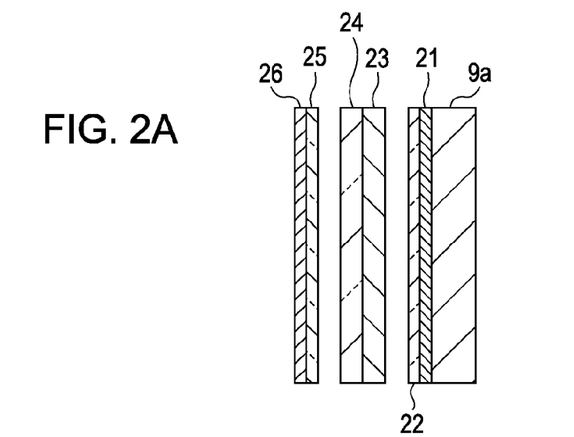
FIG. 2 illustrates optical members in front of an imaging device.
Figure 2B:
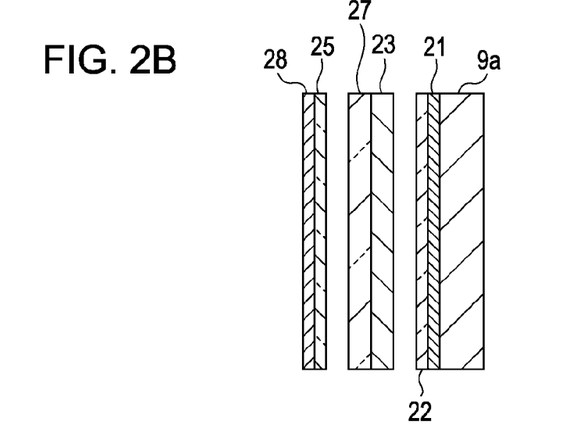
Figure 2C:
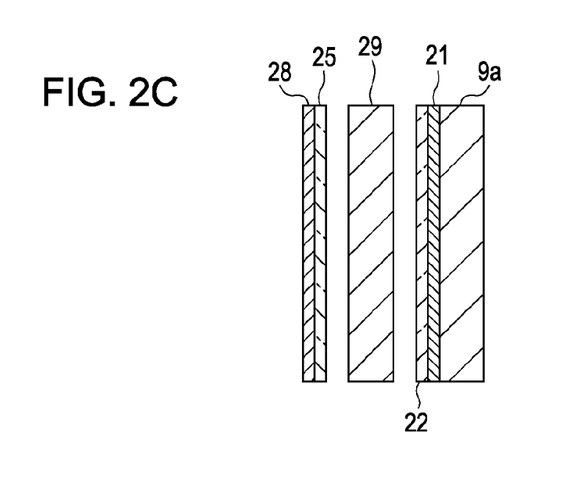

FIGS. 2A to 2C illustrate the configuration of optical members disposed in front of the image sensor 9a. FIG. 2A illustrates a configuration example of optical members in a regular digital single-lens reflex camera for visible-light imaging. Since the regular digital single-lens reflex camera includes an infrared blocking filter, the camera functions as a visible-light imaging apparatus that is only capable of capturing visible-light images.

A color filter 21 is secured on the chip of the image sensor 9a such that one of the colors RGB covers each pixel. The colors RGB are arranged in a Bayer pattern. A first crystal plate 22, which also serves as a cover glass, is secured on the front surface of the image sensor 9a. The image sensor 9a, the color filter 21, which transmits only light of a predetermined wavelength, and the first crystal plate 22 are integrated into a single unit.

A phase plate 23, which is ¼ wavelength plate for causing a phase difference, and an infrared absorption glass 24 that prevents infrared light from reaching the image sensor 9a are disposed in front of the integrated unit. A second crystal plate 25 is disposed in front of the infrared absorption glass 24. Infrared reflection coating 26 that reflects infrared light is applied to the front surface of the second crystal plate 25. In FIG. 2, the infrared reflection coating 26 appears thick. The actual thickness, however, is 1 µm or smaller.

The first crystal plate 22, the phase plate 23, and the second crystal plate 25 form an optical low-pass filter that prevents moire due to high-frequency components. Infrared light does not reach the image sensor 9a since the infrared absorption glass 24, which reduces infrared light, and the infrared reflection coating 26 block infrared. Thus, in this way, a regular digital single-lens reflex camera serves as a visible-light imaging apparatus.

Various silicon semiconductors, such as CMOSs and CCD sensors, may be used as the image sensor 9a. When the image sensor 9a is provided independently without a filter, it is sensitive to not only visible light but also near-infrared light. The pigment used in at least R (which transmits red light) of the color filter 21 generally transmits near-infrared light. Thus, the image sensor 9a provided with the color filter 21 is sensitive to infrared light. Infrared light is blocked or reduced by the infrared absorption glass 24 and the infrared reflection coating 26, as described above.

FIG. 2B illustrates the optical members in the digital single-lens reflex camera 9 according to this embodiment. The infrared absorption glass 24 and the infrared reflection coating 26 are removed to eliminate the infrared blocking or reducing ability, and instead, dummy glass 27 that compensates the optical path length of the infrared absorption glass 24 is provided. The thickness of the infrared absorption glass 24 may be substantially the same as the thickness of the infrared absorption glass 24. The optical path lengths of the infrared absorption glass 24 and the dummy glass 27 are substantially the same. Here, "substantially the same" means that a slight difference is allowable so long as the requirements of a flange back test, described below, are met. Instead of the infrared reflection coating 26, reflection prevention coating 28 that transmit near-infrared light is applied to the front surface of the second crystal plate 25. In this way, infrared light reaches the image sensor 9a, which is sensitive to infrared light, and the image sensor 9a acquires an optical image in infrared light as image data.

Accordingly, it is desirable that the dummy glass 27 be disposed closer to the image sensor 9a than the second crystal plate 25. This is because, it is easier to select, design, and inspect the optical members of the low-pass filter, i.e., the first crystal plate 22, the second crystal plate 25, and the phase plate 23, when optical-path length compensation is provided for a light flux having a narrowed wavelength band.

FIG. 2C illustrates another example of optical-path length compensation. Instead of the dummy glass 27 and the phase plate 23 in the optical member illustrated in FIG. 2B, the optical members illustrated in FIG. 2C includes a phase plate 29 that has a thickness equal to the thickness of the phase plate 23 increased by the optical path length of the infrared absorption glass 24. The optical member illustrated in FIG. 2C is advantageous in that the phase plate 23 and the dummy glass 27 illustrated in FIG. 2B are replaced with a single component, i.e., phase plate 29.

The above-described optical-path length compensation is not essential since equivalent compensation is possible by the optical system in the fundus camera 1 outside the digital single-lens reflex camera 9. However, providing optical-path length compensation in front of the image sensor 9a is desirable because it enables the use of a typical adjustment tool for a regular digital single-lens reflex camera. Since the dummy glass 27 is provided instead of the infrared absorption glass 24, the imaging optical path length is changed by the same amount as the infrared absorption glass 24. Thus, the optical path length of the imaging light inside the digital single-lens reflex camera 9 becomes the same as that of a regular digital single-lens reflex camera for visible-light image capturing. In this way, the focusing process and other processes that have different inspection and adjustment results depending on the optical path length can be integrated into a common step.

Furthermore, the thickness of the phase plate 29 is set such that the optical path length is changed by the same amount as the infrared absorption glass 24, and the optical path length of the imaging light inside the digital single-lens reflex camera 9 is set such that it is substantially the same as that of a regular digital single-lens reflex camera for visible-light imaging. In this way, the number of components can be reduced, and the processes can be integrated into a common step. The optical path lengths do not have to be identical and may be different by an amount that is allowable in the production.

Such optical path length compensation is possible by changing the positions of the image sensor 9a and other optical members, without providing additional optical members, such as the dummy glass 27. When the optical path length is compensated without providing any additional optical members, the number of components can be reduced, and thus costs can also be reduced. On the other hand, there is also a significant advantage in compensating the optical path length by providing an additional optical member. By adding an optical member, the digital single-lens reflex camera according to this embodiment can be designed and produced by partially modifying an existing digital single-lens reflex camera. Generally, the components inside the camera are disposed at optimal positions to minimize the size. Therefore, it is not easy to design an optimal camera by changing the positions of components. To change the positions of the optical members, additional steps of production, inspection, and/or adjustment need to be carried out. Such additional steps may cause a greater increase in costs than changing the number of components. By disposing an optical member that compensates the optical path length of the infrared absorption glass 24 at the position where the infrared absorption glass 24 is disposed in an existing camera, existing component positions can be maintained to achieve a design that minimizes an increase in costs. Optical-path length compensation by providing an additional optical member is advantageous in this way.

Next, the operation of the components according to this embodiment will be described with reference to the flow charts in FIGS. 3 to 5. First, the operation of the fundus camera 1 will be described with reference to FIG. 3. When the operation starts upon turning on power, initialization of the internal state of the fundus camera 1 is carried out in Step S1. Next, in Step S2, the fundus camera 1 waits for a switch to be operated. Step S2 is repeated until a switch is operated. Once a switch is operated, the process proceeds to Step S3 in which the operated switch is determined.

Subsequently, in Step S4, it is determined whether or not the operated switch is the release switch 19. When it is determined that the operated switch is not the release switch 19, the process proceeds to Step S5 to carry out internal processing of the fundus camera 1 corresponding to the operated switch. Then, the process returns to Step S2.

In Step S4, when it is determined that the release switch 19 is operated, the process proceeds to Step S6, and the infrared blocking filter 15 is inserted into the imaging optical path by the driving circuit 13 and the actuator 14. Then, the process proceeds to Step S7 in which a release signal is transmitted to the control unit 9b of the digital single-lens reflex camera 9. Then, in Step S8, the fundus camera 1 waits for a predetermined amount of time to match the timing of opening the shutter for image capturing by the digital single-lens reflex camera 9 and the timing of illuminating the imaging light source 7. After a predetermined amount of time, the process proceeds to Step S9 in which the imaging light source is illuminated for image capturing. Then, in Step S10, the infrared blocking filter 15 is retracted from the imaging optical path by the driving circuit 13 and the actuator 14. In Step S11, the strobe of the imaging light source 7 is recharged. Then, the process returns to Step S2.

As described above, in the digital single-lens reflex camera 9, the dummy glass 27 or the phase plate 29, which is each a second optical member, is provided instead of the infrared absorption glass 24, which is a first optical member. In addition, the infrared blocking filter 15, which is a third optical member having the same characteristic (spectral characteristic) as the first optical member, is provided inside the fundus camera 1. In this way, image capturing by the digital single-lens reflex camera 9, which does not have an infrared blocking filter, is possible by inserting the infrared blocking filter 15 into the optical path for examination image capturing in infrared light and by retracting the infrared blocking filter 15 from the optical path for image capturing in visible light. By setting the infrared blocking filter 15 disposed inside the fundus camera 1 to have substantially the same spectral characteristic as that of the infrared absorption glass 24 removed from the digital single-lens reflex camera 9, a spectral characteristic substantially the same as that of a regular digital single-lens reflex camera for visible-light imaging can be acquired. In this way, image processing and image capturing using the settings for a regular digital single-lens reflex camera for visible-light imaging is possible.

Next, the operation process of the computer 20 will be described with reference to FIG. 4. Upon turning on the power of the computer 20, an inquiry about the model name is sent to the digital single-lens reflex camera 9 in Step S12. In Step S13, the computer 20 waits for a response to the inquiry about the model name. When the computer 20 receives a response, the process proceeds to Step S14 in which development parameters for examination corresponding to the model name received in Step S13 is read out and the development parameters for examination are sent to the digital single-lens reflex camera 9. In this way, the development parameters for examination are set in the digital single-lens reflex camera 9.

Next, in Step S15, development parameters for imaging corresponding to the model name are read out from the computer 20 in the same manner as in Step S14; the development parameters for imaging are sent to the digital single-lens reflex camera 9; and the development parameters for imaging are set in the digital single-lens reflex camera 9.

By switching the development parameters in Steps S14 and S15, examination and image capturing optimal to the examination light source 2 and the imaging light source 7 are possible even though the light sources differ, i.e., the examination light source 2 is an infrared LED and the imaging light source 7 is a xenon tube.

In Step S16, live view is started for the digital single-lens reflex camera 9, and the operation according to this embodiment of the present invention ends.

The computer 20 carries out communication between the fundus camera 1 and the digital single-lens reflex camera 9 and transmits the model name and setting information for image processing corresponding to the model of the digital single-lens reflex camera 9. In this way, image processing corresponding to the connected digital single-lens reflex camera 9 is possible. Unlike images captured by typical consumer cameras, the images captured by a fundus camera or a digital camera connected to the fundus camera are used for medical diagnosis. Therefore, it is a problem if the color and contrast of an image influenced by the characteristic of the camera. By storing setting information for image processing in the computer 20 linked to the fundus camera 1, image processing corresponding to the characteristic of the fundus camera 1 is possible even when different models of digital cameras are connected.

Next, the operation of the digital single-lens reflex camera 9 will be described with reference to FIG. 5. Upon turning on the power, in the Step S21, the digital single-lens reflex camera 9 waits for the computer 20 to request or confirm its model name, as described in Step S12 illustrated in FIG. 4. When the model name is requested or confirmed, the process proceeds to Step S22, and the model name is sent is response to the request. The response does not necessarily have to be the actual model name but may be information for specifying the setting information of image processing, as described below.

In Step S23, the digital single-lens reflex camera 9 waits to receive from the computer 20 development parameters for examination corresponding to its model. The received development parameters for examination are stored in the memory inside the control unit 9b.

Then, in Step S25, the digital single-lens reflex camera 9 waits to receive from the computer 20 development parameters for imaging corresponding to its model. The received development parameters for imaging are set in the memory inside the control unit 9b.

Figure 4:
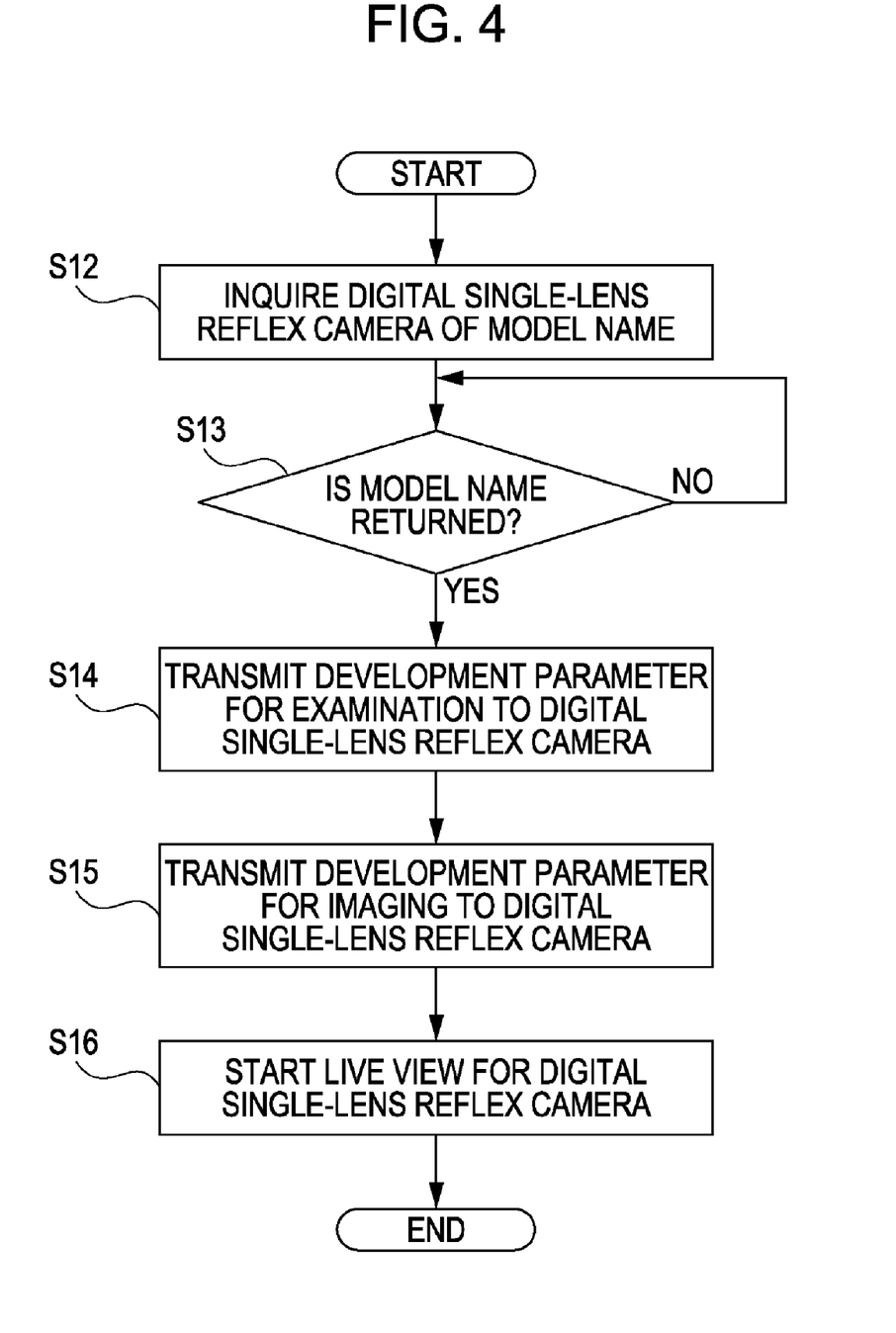
FIG. 4 illustrates a flow chart illustrating the operation of a computer.
Figure 5:
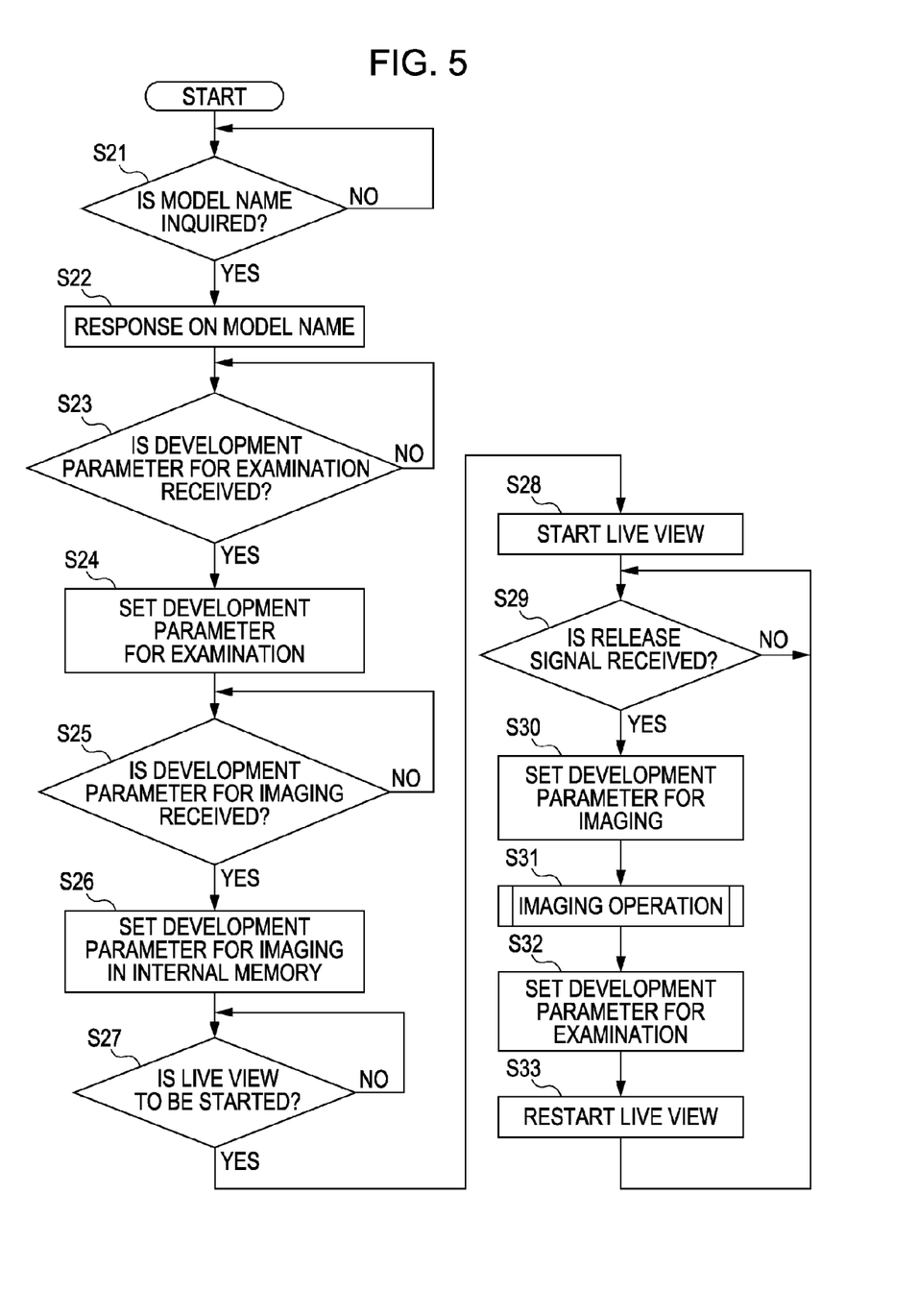
FIG. 5 illustrates a flow chart illustrating the operation of a digital single-lens reflex camera.

Then, the process proceeds to S27 in which the digital single-lens reflex camera 9 waits to receive a live view start instruction from the computer 20, as described in Step S16 illustrated in FIG. 4. Upon receiving the instruction, live view operation is started in Step S28 to use the digital single-lens reflex camera 9 as an examination unit. That is, the examination light source 2 is illuminated; the quick return mirror inside the digital single-lens reflex camera 9 is retracted; the shutter is opened; images of the ocular fundus formed on the image sensor 9a are read out in sequence; the images are developed using the development parameters for examination; and the developed images are displayed on the liquid crystal display 9c. Such operation is continued while live view is being performed.

Figure 3:
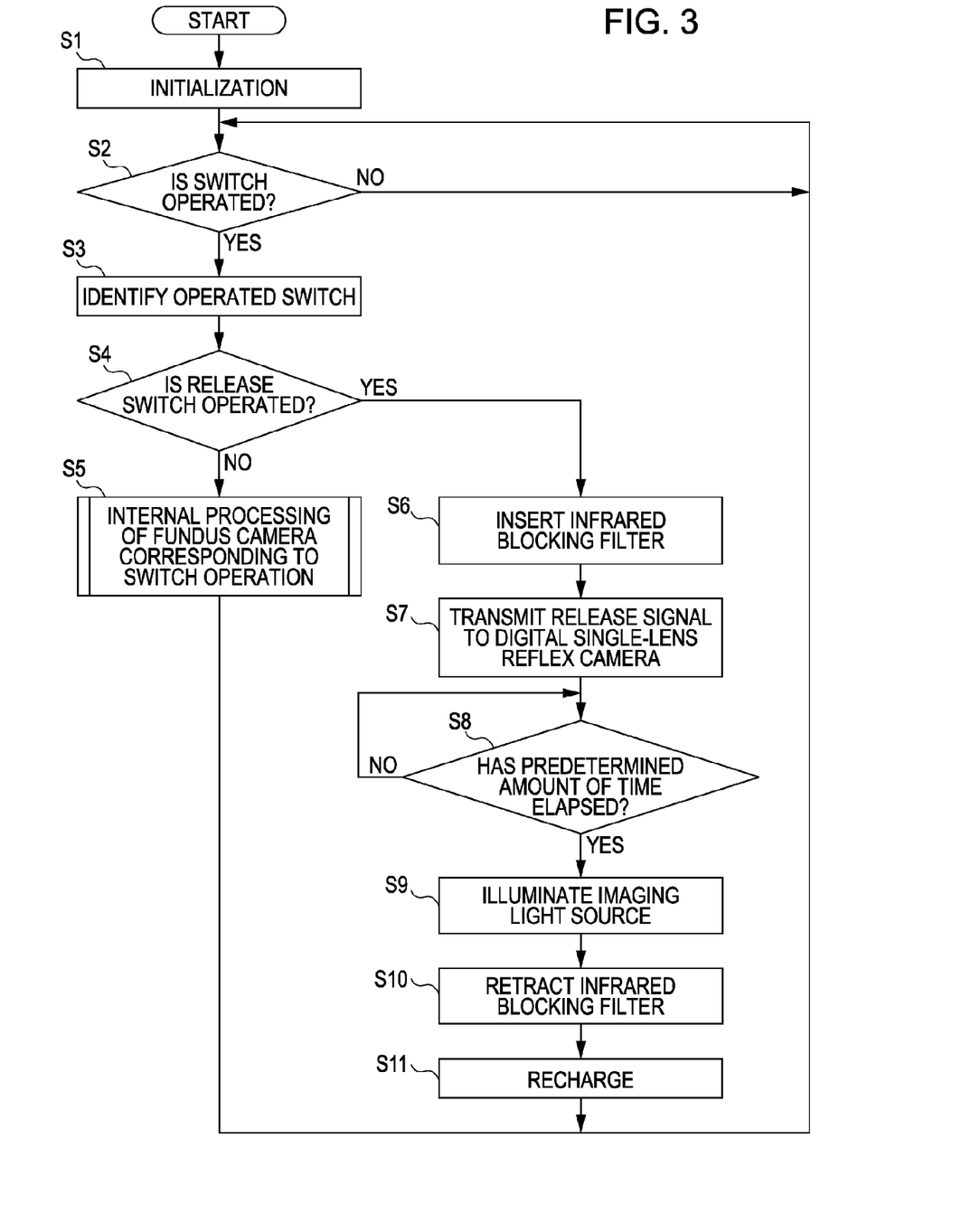
FIG. 3 is illustrates a flow chart illustrating the operation of a fundus camera.

Then, the process proceeds to Step S29 in which the digital single-lens reflex camera 9 determines whether or not it received a release signal, as described in Step S7 illustrated in FIG. 3, from the fundus camera 1. When a release signal is not received in Step S29, Step S29 is repeated. When a release signal is received, the process proceeds to Step S30 in which the development parameters for imaging set in the memory of the control unit 9b are set as the development parameters by a parameter switching unit.

Then, in Step S31, image capturing of a still image is carried out, and accumulation for the still image is carried out for a predetermined amount of time on the image sensor 9a. While carrying out accumulation, the imaging light source 7 is illuminated in Step S9 illustrated in FIG. 3, and image capturing is carried out. Then, the still image is read out; the read-out still image is developed using the development parameters for imaging; and the developed image is recorded on a storage medium (not shown) in the digital single-lens reflex camera 9. Instead, the developed still image may be sent to the connected computer 20.

When still images capturing ends, the process proceeds to Step S32 in which the development parameters for examination are set as the development parameters again. Then, in Step S33, live view is resumed, and the process returns to Step S29.

In this way, since images can be displayed and captured in accordance with the setting information of the fundus camera 1 from the computer 20, examination or capturing of ocular fundus images is possible through operation similar to that of a regular digital camera. By switching from image processing settings for adjusting infrared-light images for examination to image processing settings for adjusting visible-light images in response to the release switch being pushed, processing corresponding to an image of interest is possible without requiring a user to change the settings.

Figure 6:
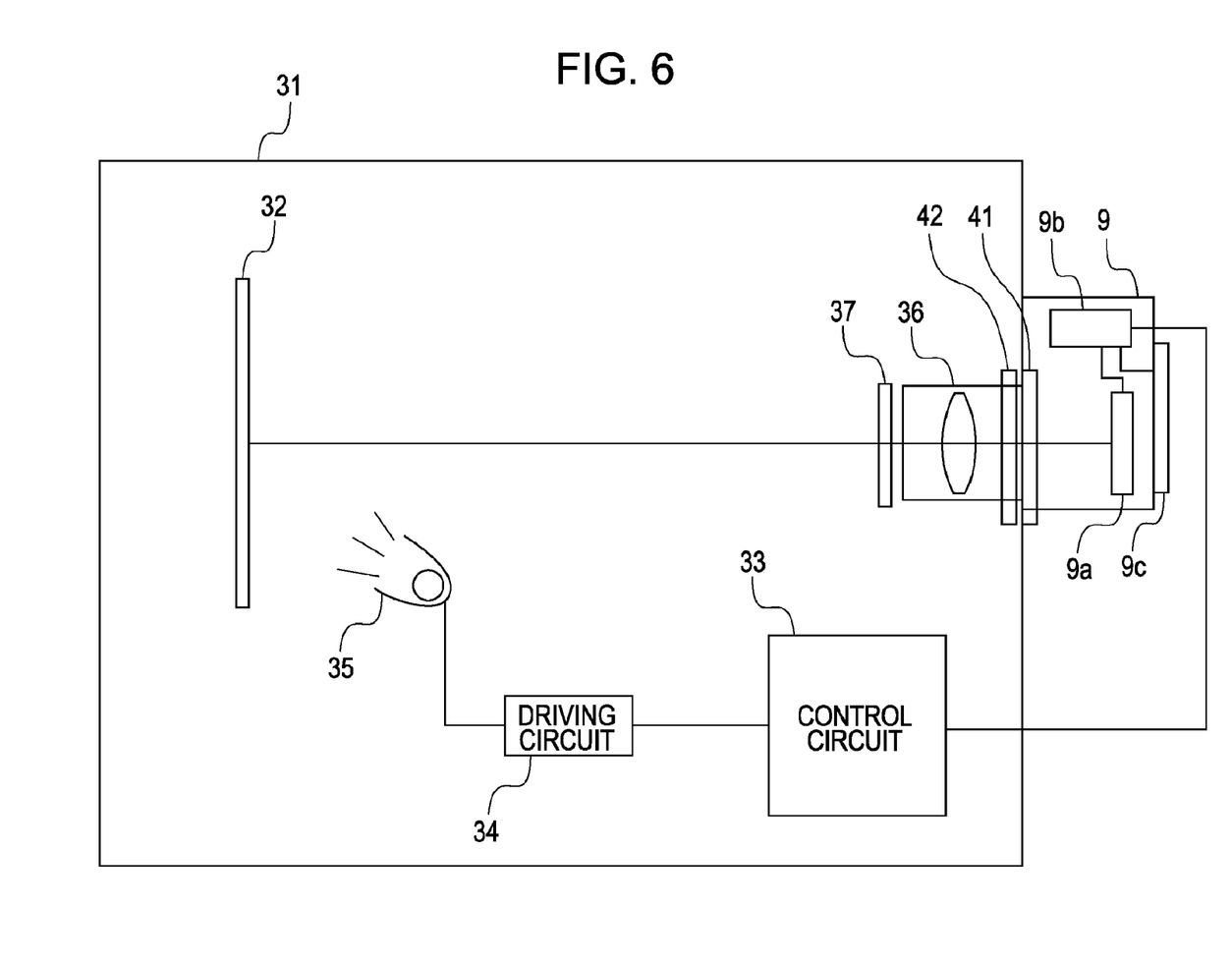
FIG. 6 illustrates an adjustment tool of the digital single-lens reflex camera.

A tool used for adjusting color balance of the digital single-lens reflex camera 9 and color balance adjustment according to this embodiment will be described below with reference to FIG. 6. Since the digital single-lens reflex camera 9 according to this embodiment does not block infrared light, the spectral characteristic differs from that of a regular digital single-lens reflex camera for visible-light imaging. Therefore, the color-balance adjustment process for a regular digital single-lens reflex camera cannot be directly applied to the digital single-lens reflex camera 9 according to this embodiment. However, costs will increase significantly if a special color-balance adjustment tool for a digital single-lens reflex camera used as a fundus camera is to be fabricated. To avoid such increase in costs, an adjustment tool for a regular digital single-lens reflex camera will be applied described below. The difference in optical path lengths does not influence color balance adjustment.

The color-balance adjustment process for the digital single-lens reflex camera according to this embodiment will be described with reference to FIG. 6. FIG. 6 illustrates an adjustment tool to which the digital single-lens reflex camera 9 is installed. Reference numeral 31 represents an adjustment tool for the digital single-lens reflex camera 9. A tool lens 36 is embedded in the adjustment tool 31. The digital single-lens reflex camera 9 can be attached to the adjustment tool 31 by the lens joining unit 41 and a lens mounting part of the tool lens 36.

The adjustment tool 31 accommodates a color chart 32 for color balance adjustment on the optical axis of the tool lens 36. The color chart 32 is an image subject of the digital single-lens reflex camera 9.

A control circuit 33 that controls the adjustment process is embedded in the adjustment tool 31. The output of the control circuit 33 is connected via a driving circuit 34 to an illumination light source 35 that illuminates the color chart 32, which is the image subject.

The control circuit 33 is also connected to the digital single-lens reflex camera 9 via a USB terminal and a special terminal used for the adjustment.

An infrared blocking filter 37 is disposed in front of the tool lens 36. The infrared blocking filter 37 is an optical filter that has a spectral characteristic substantially the same as that of the infrared blocking filter 15 in the fundus camera 1. In other words, the infrared blocking filter 37 has a spectral characteristic that provides an infrared blocking ability substantially the same as that eliminated from the digital single-lens reflex camera 9.

The infrared blocking filter 37 may be positioned manually by the user. In such a case, an insertion slot, which is an insertion unit for inserting the infrared blocking filter 37 into an optical path, may be provided in the adjustment tool 31 so that the user can insert and retract the infrared blocking filter 37. Instead, the infrared blocking filter 37 may be automatically inserted into the optical path. In such a case, the infrared blocking filter 37 is coupled with a driving mechanism, which is an insertion unit. The driving mechanism, which is the insertion unit, may be started up and inserted into or retracted from the optical path in accordance with the input information indicating whether the subject of adjustment is a regular digital single-lens reflex camera, which is a visible-light imaging apparatus, or the digital single-lens reflex camera 9 according to this embodiment. Instead, either insertion or retraction may be carried out automatically. That is, the adjustment tool 31 may function as an insertion unit that inserts the infrared blocking filter 37 into the optical path.

When a regular digital single-lens reflex camera, which is a visible light imaging apparatus, is to be adjusted, the infrared blocking filter 37 is not provided.

When adjusting the digital single-lens reflex camera 9 according to this embodiment, the infrared blocking filter 37 is dispose inside the adjustment tool 31 to carry out the adjustment process.

The production process of the digital single-lens reflex camera 9 according to this embodiment will be described below with reference to FIG. 7.

In the steps before Step S71, components are assembled according to a known production process of a digital single-lens reflex camera. The components may be assembled using a production machine or manually by an operator. In Step S71, the phase plate 29 having an increased thickness, as described above, is installed.

In the prior steps, the dummy glass 27 may be dispose in a case accommodating the infrared absorption glass 24 by adding a production line or a production step that is to be carried out simultaneously with the step of installing the infrared absorption glass 24. Instead, phase plates may be installed in two different steps; in one step, the phase plate 23 for normal visible-light imaging may be disposed, and, in the other step, another phase plate having a different thickness for the camera according to this embodiment may be disposed. In such a case, if production is not carried out on a produce line using, for example, a conveyer belt, unnecessary steps can be eliminated when modification of the step corresponding to each lot is easy.

In Step S72, the second crystal plate 25 coated with reflection prevention coating 28, which transmits near-infrared light, is mounted in the case of the camera. The position of the second crystal plate 25 in the digital single-lens reflex camera 9 is the same as that of the second crystal plate 25 in a regular digital single-lens reflex camera, as illustrated in FIG. 2. Different coating, however, is applied to each second crystal plate 25.

Other necessary components are installed in the case (Step S73). Such step is the same as that in a production process for a known digital single-lens reflex camera.

Assembly of the components is completed in this step. In subsequent steps, information for inspection and other required information are stored.

In Step S74, a flange back test is performed. A flange back in a camera with interchangeable lenses is the optical path from the mounting surface of the lens mount to the image sensor surface. Normally, the flange back length is precisely determined by the specification of the lens mount. Since a high level of precision is required for the flange back length, the flange backs in a regular digital single-lens reflex camera and the digital single-lens reflex camera 9 according to this embodiment should be precisely adjusted. The flange back test is performed using a predetermined adjustor on the basis of a known method. As a result of the flange back test, when it is determined that requirements are met, the process proceeds to S75, whereas when it is determined that requirements are not met, the result is determined to be no good.

In Step S75, preparation for the adjusting step is carried out. The infrared blocking filter 37 is inserted into the imaging optical path in the above-described adjustment tool 31. The infrared blocking filter 37 may be inserted by a driving mechanism (not shown) in the adjustment tool 31 or may be manually inserted by an operator into an insertion slot provided in advance. Here, the digital single-lens reflex camera 9 is connected to the adjustment tool 31. When connected, identification information for the digital single-lens reflex camera 9 is sent to the adjustment tool 31 via the control circuit 33. Here, identification information is information related to the functions of the connected digital single-lens reflex camera 9, which is information sufficient for specifying functions required for color balance adjustment. By sending such identification information, the reference values for adjustment are changed in accordance with the connected camera. By preparing the setting information by sending identification information corresponding to the model in this way, adjustment of several different types of cameras will be possible using a single adjustment tool 31. Moreover, there is no need to manually change the reference numeral each time the lot changes. Although the reference values are set by the operator in advance for each model, once the reference values are set, the reference values do not need to be set again for the same model.

In Step S76, color tone (color balance) is adjusted using the adjustment tool 31. In the color-balance adjustment step, the color balance of a visible-light image captured by the digital single-lens reflex camera 9 is adjusted, where the digital single-lens reflex camera 9 can capture imaging light, i.e., infrared light and visible light, as digital data. Since the adjustment tool 31 includes the infrared blocking filter 37 having the same characteristic as that of the infrared blocking filter 15, the color tone of an image acquired through visible-light imaging carried out by the fundus camera 1 can be adjusted. Gain adjustment values required for adjustment are acquired by the adjustment tool 31 and are stored in a storage unit (not shown) in the digital single-lens reflex camera 9. Details will be described below.

In Step S77, the color-balance adjusted digital single-lens reflex camera 9 is attached to the fundus camera 1. At this time, the gain adjustment values are stored in a storage unit in the computer 20 linked to the fundus camera 1. The adjustment values are stored on the side of the fundus camera 1 to carry out image processing and adjustment on images captured by the digital single-lens reflex camera 9 at the computer 20 of the fundus camera 1. Color-tone adjustment required by the fundus camera 1 is carried out using such set values. Then, the production process ends.

In this way, since the digital single-lens reflex camera 9 is connected to the fundus camera 1 after being adjusted independently, the digital single-lens reflex camera 9 can be adjusted highly precisely in accordance with the characteristics of the imaging device and optical system, without being influenced by the optical system of the fundus camera 1. Since the adjustment tool 31 includes an infrared blocking filter having the same ability as that of the fundus camera 1, the color balance does not need to be adjusted after the digital single-lens reflex camera 9 is connected with the fundus camera 1.

Detailed operation of the control circuit 33 in Step S76 of color balance adjustment will be described with reference to the flow chart illustrated in FIG. 8.

Figure 8:
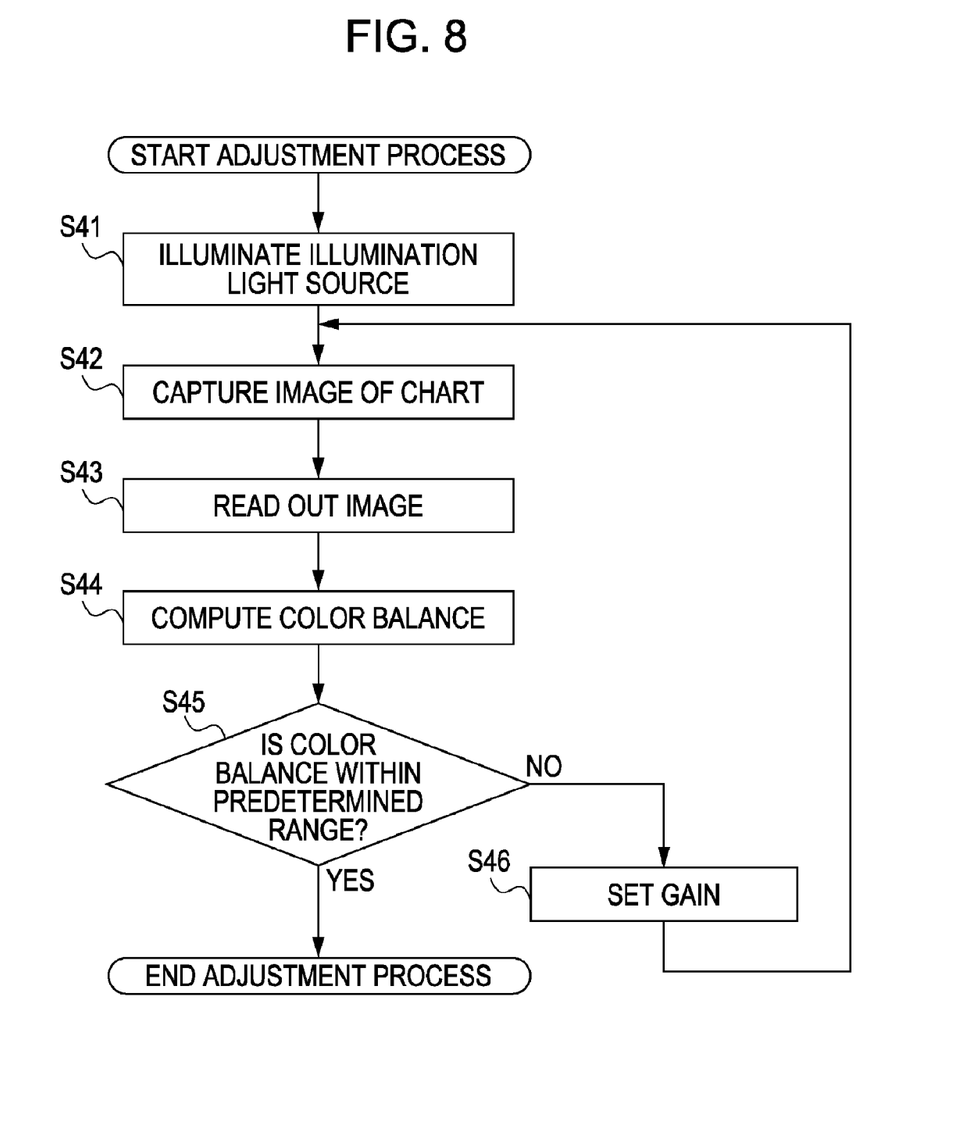
FIG. 8 is a flow chart illustrating an adjusting step of the digital single-lens reflex camera.

The flow in FIG. 8 starts upon attaching the digital single-lens reflex camera 9 to the adjustment tool 31 and starting the adjustment process.

The control circuit 33 illuminates the illumination light source 35 via the driving circuit 34 (Step S41). Next, the control circuit 33 captures the color chart 32, which is an image subject, by carrying out imaging operation of the digital single-lens reflex camera 9 (Step S42).

Next, the control circuit 33 reads out the captured image (Step S43) and computes the color balance on the basis of RGB values of the captured color chart area (Step S44). When the color balance value is within a predetermined range (Step S45), the adjustment process ends. When the color balance value is outside a predetermined range, gain values that keep the color balance value within the predetermined range are computed for the colors RGB. Then, the computed gain values are sent to the digital single-lens reflex camera 9 as adjustment values so as to carry out gain settings (Step S46).

Then, the process returns to Step S42, and color balance is adjusted by repeating Steps S42 to S46 until the color balance value is within the predetermined value.

In this way, color balance adjustment of the digital single-lens reflex camera 9 is possible. By combining the digital single-lens reflex camera 9 and the infrared blocking filter 37, the spectral characteristic of the digital single-lens reflex camera 9 becomes substantially the same as that of a regular digital single-lens reflex camera, and adjustment of the digital single-lens reflex camera 9 becomes possible without using special adjustment tools. The predetermined values used for adjustment may also be the same as those for a regular digital single-lens reflex camera.

In this embodiment, the infrared blocking filter 37 is disposed in front of the tool lens 36. Instead, however, the infrared blocking filter 37 may be disposed at any position in the imaging optical path. For example, the infrared blocking filter 37 may be interposed between the tool lens 36 and the digital single-lens reflex camera 9 or may be disposed in front of the illumination light source 35.

Figure 10:
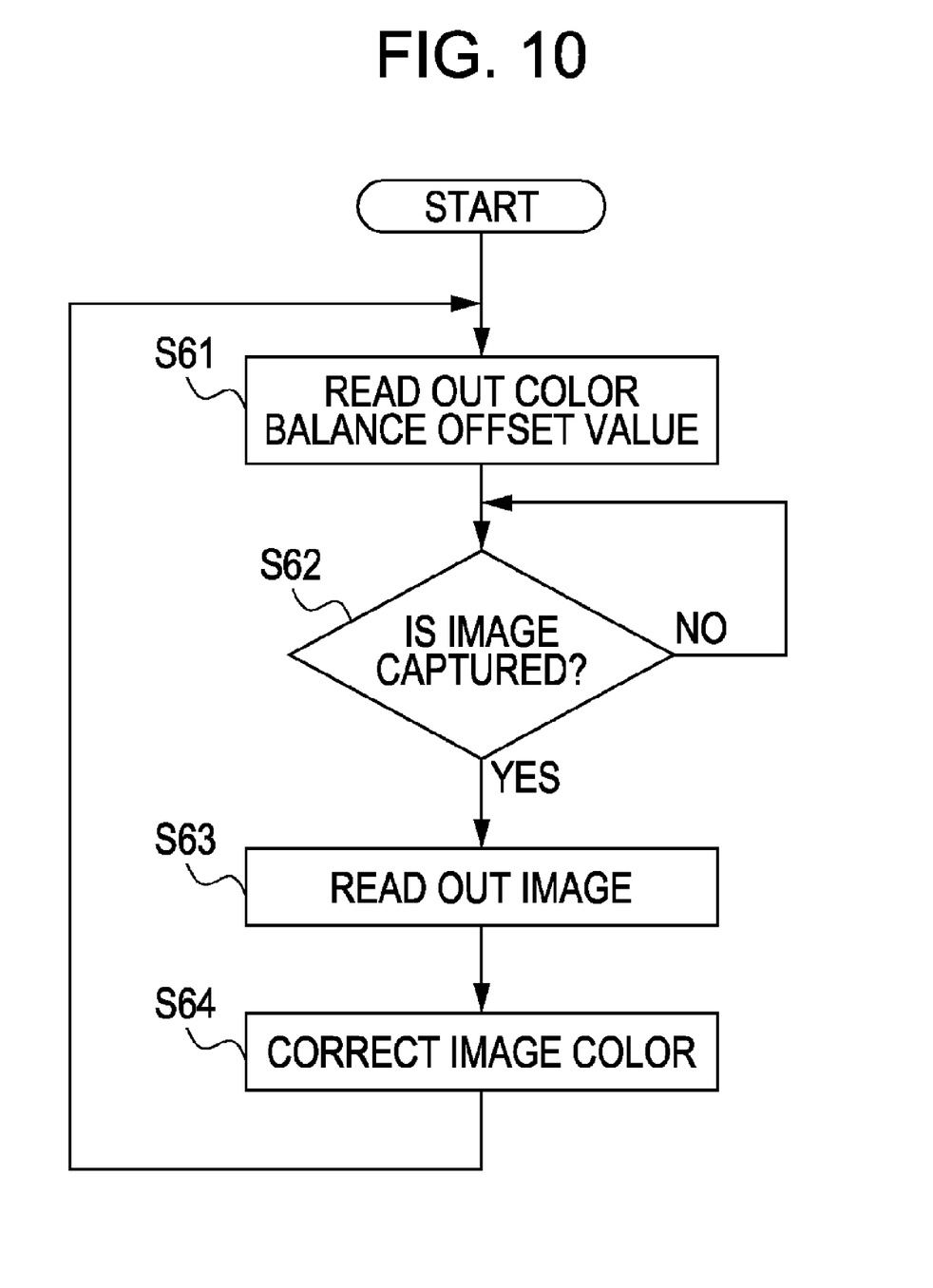
FIG. 10 is a flow chart illustrating the operation of the computer during image capturing by the fundus camera.

Next, the operation of the computer 20 during image capturing will be described with reference to FIG. 10. Prior to image capturing, the computer 20 reads out a color-balance offset value, which represents the difference between a reference value and the color balance value, from the fundus camera 1 (Step S61).

Next, in Step S62, the computer 20 waits until image capturing is performed, and when image capturing in which the image sensor 9a receives the imaging light is performed, the process proceeds to Step 63. In Step S63, the computer 20 reads out the captured image from the digital single-lens reflex camera 9.

Next, in Step S64, image color correction is performed to return the read-out image to a standard color balance based on the color-balance offset value read out in Step S61. Since the computer 20 carries out integrative control of color tone of the fundus camera 1 in this way, color balance of the image data acquired by the fundus camera 1, which is connected to the digital single-lens reflex camera 9, can be appropriately and easily adjusted.

Second Embodiment

In the second embodiment, the configuration of the apparatus and the processing carried out are the same as those according to the first embodiment, except that the configuration of the adjustment tool 31 and part of the adjustment process differ. In addition to the infrared blocking filter, the fundus camera 1 has filters that affect color tone, such as an exciter filter. An exciter filter selectively transmits light having a wavelength within a predetermined range. There is an image capturing method for the ocular fundus in which an image of a blood vessel is captured by injecting a fluorescent agent into the blood vessel and exciting the fluorescent agent by generating light that excites the fluorescent agent using the exciter filter. In such a case, an optical image is formed by light transmitted through the exciter filter that selectively transmits incident light and a light-filtering filter that selectively transmits light reflected at the ocular fundus.

To adjust white balance etc., set for image capturing, the illumination light transmitted through the exciter filter and reflected at the ocular fundus is received after transmitted through the light-filtering filter. Therefore, in this embodiment, instead of or in addition to the infrared blocking filter 37 disposed in the imaging optical path of the adjustment tool 31, an exciter filter (not shown) and a light-filtering filter (not shown) can be inserted. Such filters may be inserted manually by the user into the above-described insertion port or may be inserted automatically by an insertion unit having a driving mechanism. The adjustment process is carried out in accordance with the flow chart illustrated in FIG. 8. However, the adjustment process according to this embodiment uses an exciter filter that is not used in the adjustment process in FIG. 8, and the adjustment values are stored in a memory area different from where the adjustment values by the infrared blocking filter are stored.

In addition to the influence of the infrared blocking filter on the color tone, the influence of the exciter filter on the color can be corrected. Therefore, the color balance of image data acquired by the fundus camera can be adjusted even more appropriately.

In addition to the exciter filter, any other filter that influences the color tone of an optical system in the fundus camera may be inserted into the adjustment tool 31.

Furthermore, different development parameters of the image sensor 9a of the digital single-lens reflex camera 9 may be used for adjustment by capturing an image of the color chart 32 with the infrared blocking filter 37 inserted and for adjustment with the exciter filter inserted. Here, the development parameters are coefficient values to be multiplied with the signal values when calculating the luminance values through linear combination of the intensities of the signals acquired through the three color filters R, G, and B. When performing image capturing using an infrared blocking filter, the coefficient values may be same as those for a regular digital single-lens reflex camera for visible-light imaging. However, when an exciter filter is inserted, the coefficient values are changed. This is because when fluorography of blood vessels using a fluorescent agent is performed with the fundus camera 1, the development parameters may be changed. In this way, the color balances for fluorography can be precisely adjusted.

Another Embodiment

In this embodiment, the fundus camera 1 and the digital single-lens reflex camera 9, which are the same as those according to the first embodiment, are used. However, the purpose and the adjustment method differ from those according to the first embodiment. In this embodiment, color balance adjustment is performed on the digital single-lens reflex camera 9 independently and also while it is connected to the fundus camera 1. Since the imaging device is adjusted in advance, color tone can be adjusted highly precisely by reducing the influence of the optical system in the fundus camera 1.

The spectral characteristic of the infrared blocking filter 15 may differ from that of the infrared blocking filter 37 used in the adjustment process, although they should be the same. Such difference can be corrected as follows. The operation of the computer 20 when color balance adjustment is performed on the digital single-lens reflex camera 9 connected to the fundus camera 1 will be described with reference to FIG. 9.

In the adjustment process of the fundus camera 1, instead of the adjustment color chart 32 described above, an artificial eye model to which an adjustment color chart is attached is disposed at a position equivalent to the eye E illustrated in FIG. 1. The artificial eye model to which an adjustment color chart is attached is disposed as an image subject, and then the digital single-lens reflex camera 9 adjusted in such a manner described above is attached to the fundus camera 1. Then, the fundus camera 1, the digital single-lens reflex camera 9, and the computer 20 are connected to start the adjustment process illustrated in FIG. 8.

Figure 9:
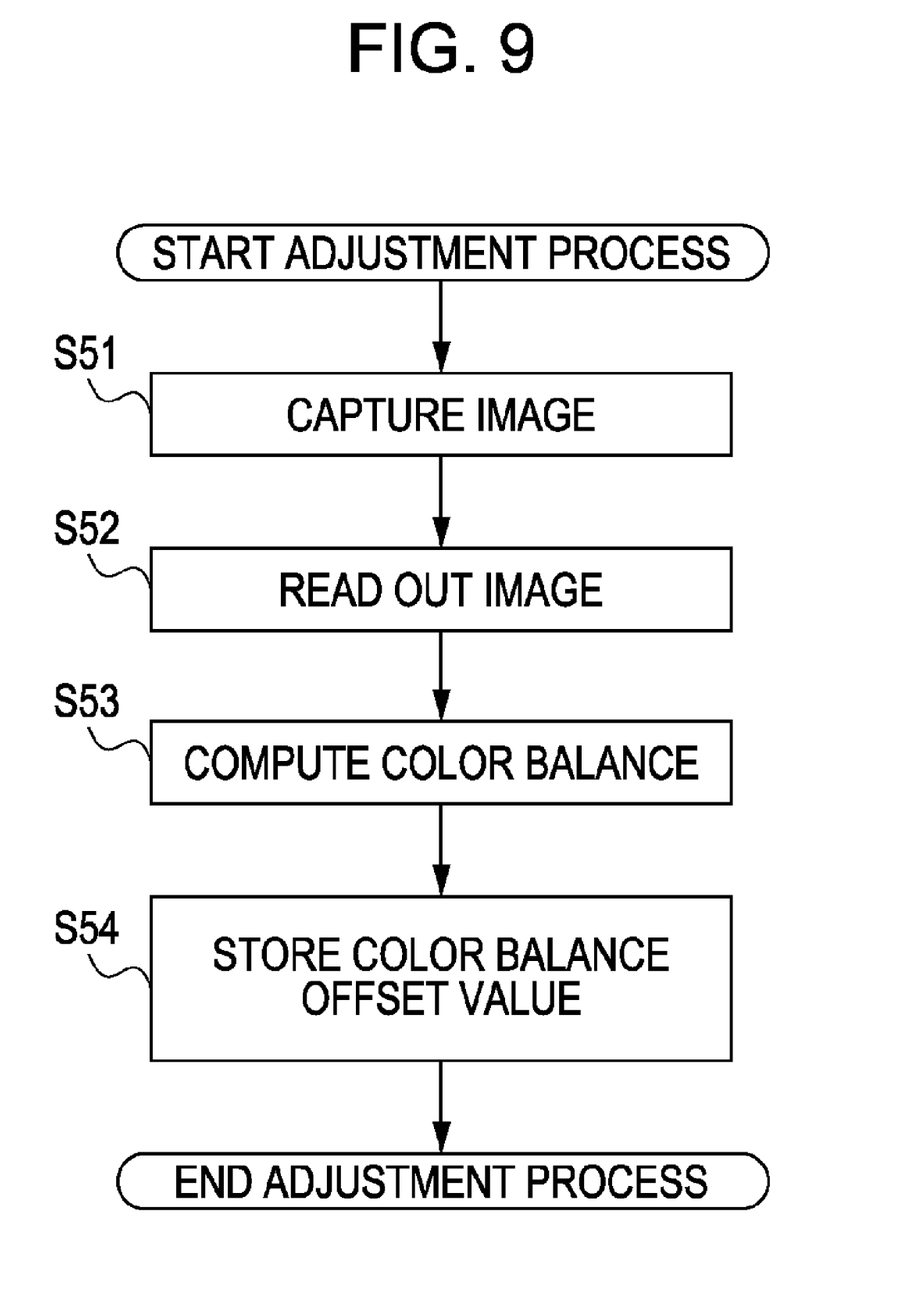
FIG. 9 is a flow chart illustrating the operation of the computer during the adjusting step of a fundus camera.

First, in Step S51, the computer 20 sends an instruction to the fundus camera 1 and the digital single-lens reflex camera 9 to carry out image capturing.

At this time, image capturing is carried out in accordance with the flow chart illustrated in FIG. 3, while the infrared blocking filter 15 is inserted.

Next, in Step S52, the computer 20 reads out the captured image from the digital single-lens reflex camera 9.

Then, in Step S53, the color balance of RGB is computed. The color balance offset value, which represents the difference between a reference value and the color balance value, is sent to the fundus camera 1 in Step S54. The fundus camera 1 stores the color balance offset value in a non-volatile memory (not shown) in the control circuit 10 or in an external device. Then, the adjustment process ends. In this way, error due to production variation of the infrared blocking filter 15 can be corrected. By adjusting the color balance of the digital single-lens reflex camera 9 independently or while connected to the fundus camera 1, even more precise adjustment is possible. In this way, the functions of the digital single-lens reflex camera can be appropriately and efficiently used.

As described above, the digital single-lens reflex camera can be used as an examination unit and an imaging unit to provide an ophthalmic imaging apparatus with high image quality, low costs, and a small size. Furthermore, focusing error does not occur since the optical path length is compensated.

Moreover, a digital single-lens reflex camera, which is an imaging unit for an ophthalmic imaging apparatus, can be produced without carrying out a special process.

The present invention is not limited to the embodiments described above, and various modifications are possible within the scope of the invention.

For example, the examination light source 2 according to the first embodiment is an infrared LED. Instead, however, as the examination light source, a combination of a light source that outputs visible light and infrared light, such as a halogen lamp, and a visible-light blocking filter may be used.

Figure 7:
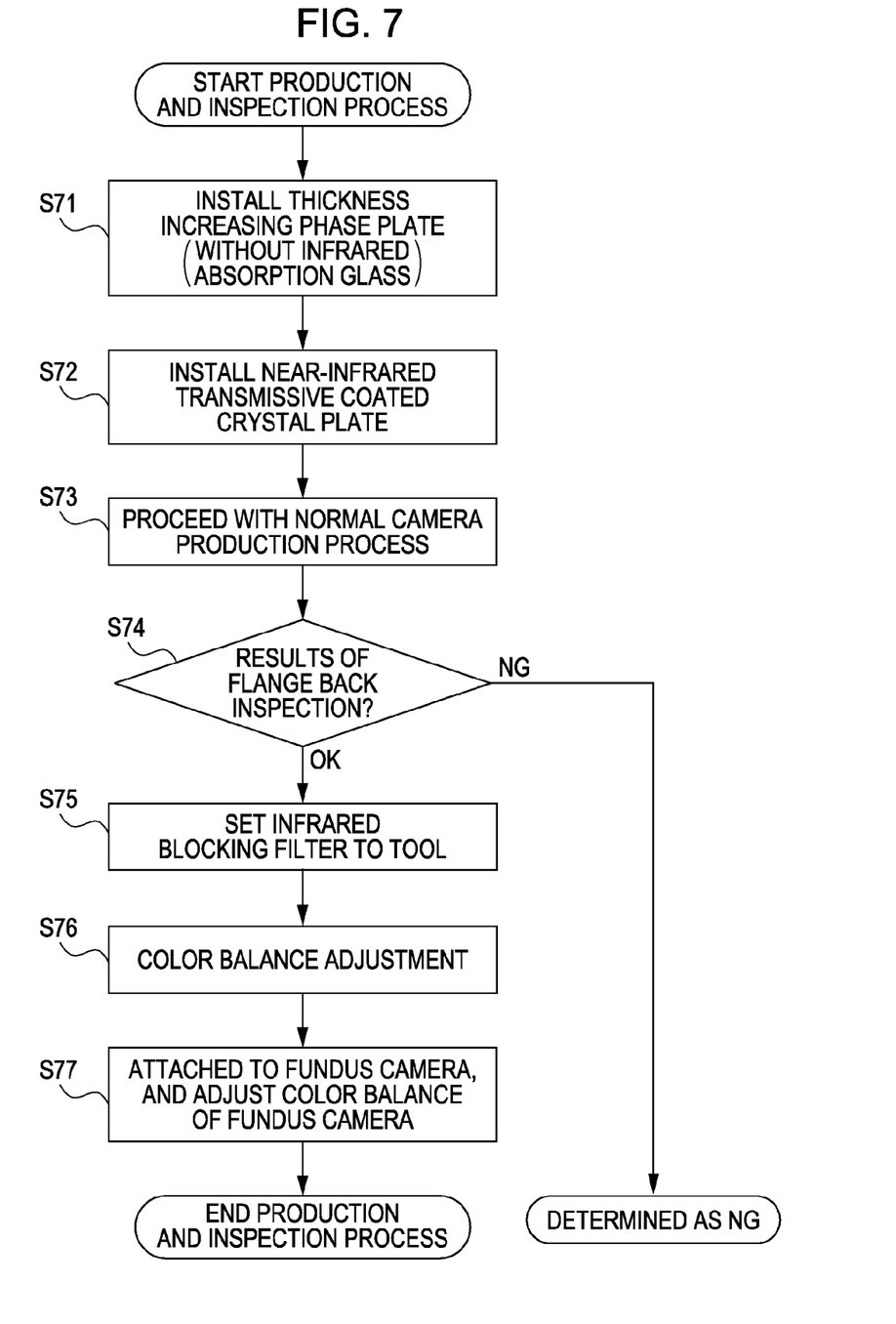
FIG. 7 is a flow chart illustrating a production step of the ophthalmic imaging apparatus according to an embodiment.

The production process illustrated in FIG. 7 may be a process of disposing a dummy glass. In such a case, first, a step of disposing the infrared absorption glass 24 at a predetermined position in the case is carried out. Then, the infrared absorption glass 24 is removed. After removal, the step of disposing the dummy glass 27 at the predetermined position is carried out. After removing the infrared absorption glass 24 disposed at the predetermined position, the phase plate 23 is also removed, and a new phase plate having an appropriate thickness is disposed.

In such a case, in addition to known steps, production steps for the camera according to this embodiment are carried out. In this way, the known steps are less likely to be affected by the production steps of the camera according to this embodiment. This embodiment is particularly advantageous when most of the components of the camera according to this embodiment are the same as those of a regular digital single-lens reflex camera, which is a viable-light imaging apparatus, and when the number of cameras to be produced is relatively small. When a production line, such as a conveyer belt, is used for production, this embodiment is advantageous in that an existing line can be efficiently used.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-241697, filed 2009 Oct. 20, which is hereby incorporated by reference herein in its entirety.

What is claimed is:

1. A method of manufacturing an ophthalmic imaging apparatus comprising the steps of:
   providing an imaging unit configured to capture image data of a subject in visible light and infrared light;
   adjusting the color tone of the imaging unit using a color-tone adjustment unit having a first optical member configured to absorb infrared light; and
   connecting the adjusted imaging unit and an optical system independent of the color-tone adjustment unit and the imaging unit having a second optical member whose characteristic is substantially the same as a characteristic of the first optical member and configured to capture an optical image of an eye to be examined.

2. The method according to claim 1, wherein in the adjusting step, a reference value of the color tone is changed in accordance with identification information of the produced imaging unit.

3. The method according to claim 1, wherein in the connecting step, an adjustment value acquired in the adjusting step is sent to the ophthalmic imaging apparatus in accordance with the connection established in the connecting step.

4. The method according to claim 1, wherein the adjustment unit includes,
   a color chart provided as an image subject of the imaging unit, and
   an insertion unit configured to insert the first optical member into an optical path of imaging light of the imaging unit capturing the color chart.

5. The method according to claim 4,
   wherein the optical system captures an optical image of a blood vessel of an ocular fundus using a first exciter filter configured to transmit light having a wavelength within a predetermined range, and
   wherein the insertion unit is configured to insert a second exciter filter having a same characteristic as a characteristic of the first exciter filter into the optical path of the imaging light.

6. The method according to claim 5, wherein a development parameter of the imaging unit is changed depending on whether the first optical member or the second exciter filter is used in the adjusting step.

7. An inspection apparatus configured to inspect a first imaging device having an imaging element sensitive to visible light and infrared light and a first optical member configured to prevent infrared light from reaching the imaging element, the inspection apparatus comprising:
   a color chart;
   an insertion unit configured to insert a second optical member into an optical path of the infrared light from the color chart to the second imaging device, the second optical member having a characteristic substantially the same as a characteristic of the first optical member; and
   a connection unit configured to connect with both the first imaging device and a second imaging device identical to the first imaging device except that the first optical member is removed,
   wherein the first imaging device, when connected with the connection unit, captures an image of the color chart and acquires a color-balance adjustment value without inserting the second optical member using the insertion unit, and the second imaging device captures, when connected with the connection unit, an image of the color chart and acquires the color-balance adjustment value by inserting the second optical member using the insertion unit.

8. The inspection apparatus according to claim 7,
   wherein the second imaging device has a connecting unit configured to connect the second imaging device to an ophthalmic imaging apparatus configured to capture an optical image of an eye to be examined, and
   wherein the color chart is disposed at a position of the eye to be examined when capturing an image by the ophthalmic imaging apparatus.

9. The inspection apparatus according to claim 7, wherein the insertion unit has a driving unit configured to insert the second optical member into the optical path.

10. The inspection apparatus according to claim 7, wherein the insertion unit includes an insertion port through which the second optical member is inserted into the optical path.

11. An ophthalmic imaging apparatus configured to capture an optical image of an ocular fundus in visible light and an optical image of an ocular fundus in infrared light, the apparatus comprising:
    a capturing unit configured to capture the optical image of the ocular fundus;
    a first crystal plate;
    a phase plate configured to transmit visible light and infrared light, adjust the optical path length of light transmitted through the first crystal plate, and change the phase of the light transmitted through the glass;
    a second crystal plate configured to transmit at least part of the light transmitted through the phase plate;
    a color filter configured to transmit light of a predetermined wavelength in the light transmitted through the second crystal plate; and
    an imaging device configured to receive the visible light and infrared light transmitted through the color filter,
    wherein the first crystal plate, the glass, the phase plate, the second crystal plate, and the color filter are disposed between the capturing unit and the imaging device in an imaging light path of the captured optical image.

12. The ophthalmic imaging apparatus of claim 11, wherein in a first mode the imaging device receives a visible light and outputs first image data, and in a second mode the imaging device receives an infrared light and outputs second image data.

13. The ophthalmic imaging apparatus of claim 12, further comprising an optical member insertable into an imaging optical path in the capturing unit,
    wherein in the first mode the optical member is inserted into the imaging optical path, and in the second mode the optical member is retracted from the imaging optical path.

14. The ophthalmic imaging apparatus of claim 12, further comprising a first light source configured to emit infrared light to illuminate an ocular fundus in the first mode; and
    a second light source configured to emit visible light to illuminate an ocular fundus in the second mode.

15. The ophthalmic imaging apparatus of claim 11, further comprising an imaging unit including the first crystal plate, the phase plate, the second crystal plate, the color filter and the imaging device, the imaging unit being attachable and detachable to the capturing unit.

16. The ophthalmic imaging apparatus of claim 15, wherein the imaging unit further including a provision unit configured to provide the capturing unit with at least one of type information of the imaging unit and setting information concerning image processing.

17. The ophthalmic imaging apparatus of claim 15, wherein in a first mode the imaging unit receives a visible light and outputs first image data, and in a second mode the imaging unit receives an infrared light and outputs second image data.

18. The ophthalmic imaging apparatus of claim 11, further comprising
   a display unit configured to display image data obtained by receiving an infrared light; and
   a storage unit configured to store image data obtained by receiving an infrared light.

19. An ophthalmic imaging apparatus comprising:
   a detachable imaging unit including
      an imaging device;
      a display unit configured to sequentially display images formed on the imaging device;
      a first optical member disposed in an imaging optical path of the imaging device, configured to transmit infrared light and visible light, and
      a second optical member insertable into an imaging optical path, configured to absorb infrared light and having an optical path length that is substantially the same as the optical path length of the first optical member.

20. An imaging unit attached to an apparatus configured to capture an optical image of an ocular fundus in a detachable manner, the unit comprising:
   an imaging device;
   a display unit; and
   a first optical member configured to transmit infrared light and visible light,
   wherein the first optical member has an optical path length substantially the same as the optical path length of a second optical member insertable into and retracted from an optical path in the apparatus, configured to absorb infrared light.

* * * * *